US008361045B2

(12) United States Patent
Thorson et al.

(10) Patent No.: US 8,361,045 B2
(45) Date of Patent: Jan. 29, 2013

(54) APPARATUS AND METHOD FOR MANUFACTURING SEVERAL DISTINCT DISPOSABLE ABSORBENT ARTICLES ON A SINGLE MACHINE

(75) Inventors: Russell Evan Thorson, Appleton, WI (US); Robert Lee Popp, Hortonville, WI (US); Joseph Daniel Coenen, Kaukauna, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1697 days.

(21) Appl. No.: 11/373,029

(22) Filed: Mar. 10, 2006

(65) Prior Publication Data
US 2007/0213678 A1    Sep. 13, 2007

(51) Int. Cl.
*A61F 13/15* (2006.01)
*A61F 13/20* (2006.01)

(52) U.S. Cl. .................. 604/385.01; 604/386; 604/387; 604/367

(58) Field of Classification Search ............. 604/385.01, 604/385.11, 385.24–385.3, 386–389; 156/250
See application file for complete search history.

(56) References Cited

U.S. PATENT DOCUMENTS

| | | | |
|---|---|---|---|
| 4,720,415 A | 1/1988 | Vander Wielen et al. | |
| 4,938,757 A * | 7/1990 | Van Gompel et al. | 604/396 |
| 5,116,662 A * | 5/1992 | Morman | 428/198 |
| 5,336,545 A | 8/1994 | Morman | |
| 5,383,988 A | 1/1995 | Herrmann et al. | |
| 5,385,775 A | 1/1995 | Wright | |
| 5,492,591 A | 2/1996 | Herrmann et al. | |
| 5,868,899 A | 2/1999 | Gundersen | |
| 6,036,805 A | 3/2000 | McNichols | |
| 6,273,165 B1 | 8/2001 | Gundersen et al. | |
| 6,454,888 B1 | 9/2002 | Murie et al. | |
| 6,463,606 B2 * | 10/2002 | Barker et al. | 5/500 |
| 6,574,520 B1 | 6/2003 | Liu et al. | |
| 6,783,487 B2 | 8/2004 | Duhm et al. | |
| 6,820,671 B2 | 11/2004 | Calvert | |
| 6,895,649 B2 | 5/2005 | Kojo et al. | |
| 2002/0119722 A1 | 8/2002 | Welch et al. | |
| 2003/0004594 A1 | 1/2003 | Liu et al. | |
| 2003/0065297 A1 | 4/2003 | Davis et al. | |
| 2003/0066594 A1 | 4/2003 | Malakouti et al. | |
| 2005/0109442 A1 | 5/2005 | Neubauer et al. | |
| 2005/0113791 A1 | 5/2005 | Neubauer et al. | |

FOREIGN PATENT DOCUMENTS

| | | |
|---|---|---|
| EP | 0 396 512 A2 | 11/1990 |
| EP | 0 875 225 A1 | 11/1998 |
| EP | 1 188 426 A2 | 3/2002 |
| EP | 1 413 430 B1 | 6/2005 |
| WO | WO 95/32695 A1 | 12/1995 |

(Continued)

*Primary Examiner* — Michele M Kidwell
(74) *Attorney, Agent, or Firm* — David J. Arteman

(57) ABSTRACT

An apparatus and a method are disclosed for manufacturing several distinct disposable absorbent articles on a single machine. The apparatus includes three sections. The first section is capable of forming an absorbent assembly and cutting the absorbent assembly into individual absorbent assemblies. The second section is capable of moving a bodyside liner into alignment with the individual absorbent assemblies and applying an outer cover to the individual absorbent assemblies to form a continuous web having a primary stretch in a cross direction. The second section is further capable of adding at least three components to the web. The third section is capable of severing the continuous web into individual absorbent articles which can then be folded, stacked and packaged.

5 Claims, 1 Drawing Sheet

FOREIGN PATENT DOCUMENTS

| WO | WO 9923984 A1 * | 5/1999 |
| WO | WO 00/37007 A1 | 6/2000 |
| WO | WO 02/32357 A2 | 4/2002 |
| WO | WO 02/32360 A2 | 4/2002 |
| WO | WO 2004/030477 A1 | 4/2004 |
| WO | WO 2004/049989 A1 | 6/2004 |

* cited by examiner

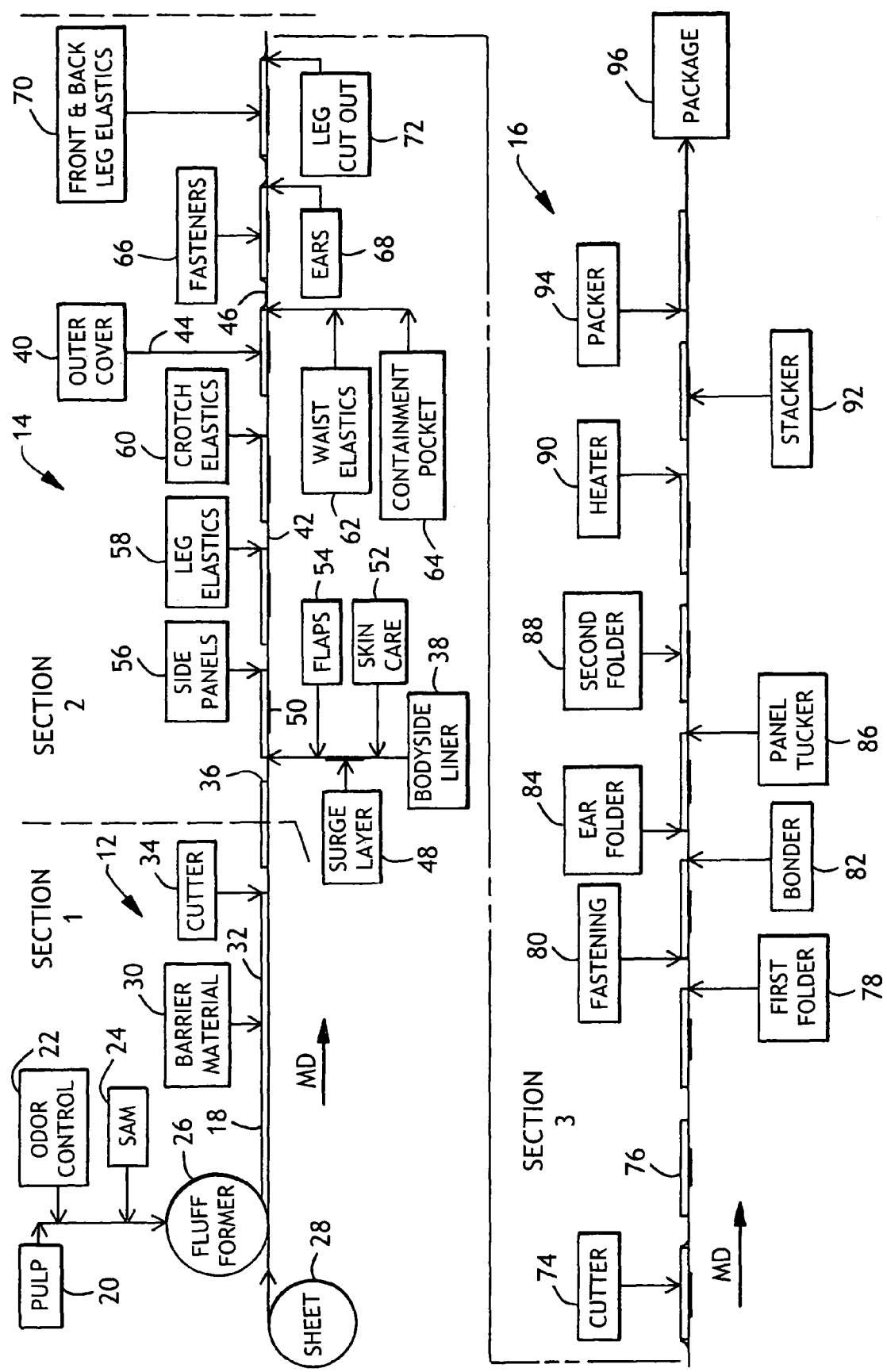

APPARATUS AND METHOD FOR MANUFACTURING SEVERAL DISTINCT DISPOSABLE ABSORBENT ARTICLES ON A SINGLE MACHINE

BACKGROUND OF THE INVENTION

Today, many different kinds of disposable absorbent articles are being manufactured on a plurality of unique machines. Disposable absorbent articles are currently being manufactured and sold for use by infants, toddlers and adults. Such disposable absorbent articles include infant diapers, child training pants, menstrual pants, adult incontinent undergarments, guards for men, briefs, etc. Many machines are limited to producing a distinct disposable absorbent article in a particular size. Some machines can be retrofitted or modified to produce a smaller or larger size disposable absorbent article but no machine has the ability to produce a variety of different absorbent articles. For example, a machine that can produce one or two sizes of infant diapers cannot easily be retrofitted to produce a refastenable adult incontinent undergarment.

Many manufacturers produce several sizes or codes of each disposable absorbent article to accommodate the various sizes, shapes, configurations and absorbency levels required by a particular set of users. For example, diapers are manufactured in various sizes to accommodate the growth of a baby. One size diaper is sized and shaped to accommodate a new born infant, while several other diapers are sized and shaped to accommodate an infant of increasing weight, torso shape and dimension. A diaper designed for an infant weighing from between about 7 to about 10 pounds will require a certain absorbency level while a diaper designed for an infant weighing from between about 10 to about 15 pounds will require a much higher absorbency level. In addition, as a baby grows, its bodily size and shape will quickly change and the waist opening, leg openings, rise of the diaper, etc., will have to change to accommodate such growth. Furthermore, the sex of the baby will also affect the design of the disposable absorbent article. For example, a diaper designed for a boy will be different from a diaper designed for a girl in that the position of the absorbent material will be skewed to match up with the genitalia of the infant.

It has long been recognized that if a machine could be invented that had the capability of manufacturing various kinds of disposable absorbent articles in various sizes, it would be welcomed by the manufacturers of such articles. Such a machine would reduce capital cost and reduce the number of spare parts that a manufacturer needs to retain. In addition, if all the machines were of essentially the same appearance and performed in a similar manner and function, one could increase operating efficiency. Furthermore, as the demand for a certain article increased, a manufacturer would be able to switch production on a single machine to meet demand using a single crew. This universal machine would also allow a manufacturer to get into new markets with a limited investment. For example, a manufacturer could startup an operation in a third world country and use the machine to produce say only infant diapers. As the market grew and demand picked up, the manufacturer could use the same machine to manufacture training pants and/or adult incontinent undergarments. Furthermore, a roll out of an improvement could be accomplished in a very short period of time at reduced cost.

Now an apparatus and a method for manufacturing several distinct disposable absorbent articles on a single machine has been invented.

SUMMARY OF THE INVENTION

Briefly, this invention relates to an apparatus and a method for manufacturing several distinct disposable absorbent articles on a single machine. The apparatus includes three sections. The first section is capable of forming an absorbent assembly having a predetermined size and shape. The second section includes a first applicator capable of moving a bodyside liner into alignment with the absorbent assembly and a second applicator capable of moving an outer cover into alignment with the absorbent assembly to form a continuous web having a primary stretch in a cross-direction. The second section further includes at least three of the following applicators: a surge layer applicator capable of positioning a surge layer within the web, a skin care applicator capable of applying a skin care formulation or composition to at least one layer of said web, a containment flap applicator capable of engaging at least one pair of containment flaps to the web, a side panel applicator capable of attaching at least one pair of side panels to the web, an elastic applicator capable of applying elastics to the web which will correspond to a crotch region, waist region, and/or leg opening regions of each of the individual absorbent articles, a fastener applicator capable of applying one or more fasteners to the web, and a cutter applicator capable of cutting leg openings in the web. The third section is capable of severing the continuous web into individual absorbent articles and then folding, stacking and packaging the absorbent articles.

The method involves the steps of activating certain applicators at a predetermined time to form several distinct disposable absorbent articles on a single machine.

BRIEF DESCRIPTION OF THE DRAWINGS

FIG. 1 is a schematic showing the various components of the apparatus and the method for manufacturing several distinct disposable absorbent articles on a single machine.

DETAILED DESCRIPTION

Referring to FIG. 1, a schematic is depicted which represents an apparatus 10 and a method for manufacturing several distinct disposable absorbent articles on a single machine. By "several" it is meant that at least three different kinds of disposable absorbent articles can be manufactured on the single machine. For example, the apparatus 10 and the method can be used to manufacture an infant diaper, a child training pant and/or an adult incontinent undergarment. These different absorbent articles can be produced in varying sizes including small, medium, large and extra large, etc. One skilled in the art will quickly recognize that a large size infant diaper will be much smaller than a large size adult incontinent undergarment. The present apparatus 10 and method is believed to be the first that will allow such a large variance in sizes and configurations of disposable absorbent articles to be manufactured on a single machine.

The apparatus 10 includes a first section 12, a second section 14 and a third section 16. The first section 12 is capable of forming an absorbent assembly 18 having a predetermined size and shape. Normally, a continuous strip of absorbent material is formed having a predetermined basis weight, width and height. The absorbent assembly 18 can be created from cellulosic pulp 20, for example wood pulp. The apparatus 10 includes an odor control applicator 22 which is capable of adding or introducing an odor control substance onto or into the cellulosic pulp 20. The odor control substance can be a liquid, a solid or a semi-solid and can consist of any substance known to those skilled in the art for masking or eliminating certain odors. Alternatively, the odor control substance can be added to a raw material prior to converting. In absorbent articles, odors from urine and excrement are the most common that need to be eliminated or masked. One odor control substance that works well at masking or eliminating such body waste odors is baking soda. The baking soda can be present in granular or particle form.

The apparatus 10 also includes a superabsorbent applicator 24 which is capable of adding or introducing a superabsorbent material 24 (SAM) into or onto the fiberized cellulosic pulp 20. A superabsorbent is a material that is capable of absorbing at least 10 grams of water per gram of superabsorbent material. The superabsorbent material can be in the shape of small particles, although fibers, flakes or other geometrical forms can also be used. A suitable superabsorbent material is FAVOR 880. FAVOR is a registered trademark of Stockhausen, Inc. having an office located at 2408 Doyle Street, Greensboro, N.C. 27406. FAVOR 880 is a commercial designation of one of Stockhausen's superabsorbents. Other similar types of superabsorbents, some of which are commercially available from Stockhausen, Inc., as well as from other known suppliers, can also be used. Desirably, the amount of superabsorbent material present in the absorbent assembly 18 will be a weight percent of from about 10% to about 90%. More desirably, the amount of superabsorbent material present in the absorbent assembly 18 will be a weight percent of from about 20% to about 80%. Even more desirably, the amount of superabsorbent material present in the absorbent assembly 18 will be a weight percent of from about 30% to about 75%.

The treated cellulosic pulp 20 is then fed into a fluff former applicator 26, also commonly referred to as a hammer mill. In the fluff former applicator 26, the treated cellulosic pulp 20 is hammered, broken and transformed into individual cellulosic fibers known as fluff or fiberized pulp. Fluff is light, soft and frothy in consistency and appearance. It should also be recognized that the odor control substance and/or the superabsorbent material can be introduced into the fluff former applicator 26. Alternatively, the odor control substance and/or the superabsorbent material can be introduced upstream or downstream of the fluff former applicator 26.

The fluff is then deposited onto a carrier sheet 28 which is moving in a machine direction, denoted as MD in FIG. 1. In FIG. 1, the machine direction is from left to right. It should be mentioned that the apparatus 10 as shown and described herein forms the absorbent article upside down. Alternatively, the absorbent article can be formed top-side up.

The carrier sheet 28 is normally a liquid permeable material, for example, a low basis weight tissue, which contains the cellulosic fibers and any superabsorbent material that may be present. The carrier sheet 28 can optionally be wrapped around at least a portion of the fluff to form an elongated absorbent assembly 18. Desirably, the carrier sheet 28 is wrapped around the fluff and abuts or overlaps itself on one of the major surfaces of the absorbent assembly. Alternatively, the carrier sheet 28 can be aligned adjacent to at least one surface of the absorbent assembly 18. Generally, the absorbent assembly 18 will have an approximately rectangular cross-sectional profile at this time. Usually, the absorbent assembly 18 will consist of one absorbent layer but it could include two or more absorbent layers, if desired. At this point, the absorbent assembly 18 can be optionally routed through a debulker (not shown) where it would be reduced in thickness.

The first section 12 of the apparatus 10 also includes a barrier material applicator 30 for introducing a barrier material 32 onto one surface of the absorbent assembly 18. In FIG. 1, the barrier material 32 is positioned on the upper surface of the absorbent assembly 18. Because the absorbent article is being constructed upside down, the barrier material 32 will be positioned away from the torso of the wearer when the absorbent article is worn. The barrier material 32 is a liquid-impermeable material which will prevent liquid; such as urine, from passing therethrough. Two materials that work well as a barrier material are polyethylene and polypropylene. The thickness of the barrier material 32 can vary but it is usually only a few microns thick. It should be noted that the barrier material 32 can be located adjacent to only one major surface of the absorbent assembly 18 or it can partially or fully wrap around the sides of the absorbent assembly 18 if desired.

The apparatus 10 can further include additional optional applicators to permanently bond one or more edges of the carrier sheet 28 and/or the barrier material 32 to the absorbent assembly 18. However, such bonding steps are not necessary to form a useable absorbent assembly 18.

The first section 12 of the apparatus 10 further includes a cutting applicator 34 which is capable of severing or cutting the absorbent assembly 18 into individual absorbent assemblies 36. Each of the individual absorbent assemblies 36 will have a predetermined size and shape. For example, each of the individual absorbent assemblies 36 can have a length ranging from between about 6 inches (about 15 centimeter (cm)) to about 30 inches (about 75 cm), a width ranging from between about 2 inches (about 5 cm) to about 16 inches (about 40 cm) and a thickness ranging from between about 0.04 inches (about 0.1 cm) to about 0.5 inch (about 1.3 cm). The exact dimensions will partly depend upon what kind and type of disposable absorbent article the absorbent assembly 18 will be a part of. The presence or amount of superabsorbent material and the actual use for which the disposable absorbent article is designed will also determine its final dimensions.

The second section 14 of the apparatus 10 includes a first applicator 38 and a second applicator 40. The first applicator 38 is capable of moving a bodyside liner 42 into alignment with the individual absorbent assemblies 36. It should be noted that in this apparatus 10, the individual absorbent assemblies 36 can be merged or aligned with the bodyside liner 42, or alternatively, the bodyside liner 42 can be brought into registration and/or alignment with one of the major surfaces of each of the individual absorbent assemblies 36. In FIG. 1, the bodyside liner 42 will be located away from the barrier material 32. The second applicator 40 is capable of moving an outer cover 44 into registration with the opposite major surface of each of the individual absorbent assemblies 36. The second applicator 40 can also be constructed so as to apply the outer cover 44 to the absorbed assembly 36. In other words, the bodyside liner 42 will be located on one side of the individual absorbent assemblies 36 and the outer cover 44 will be located on the opposite side of the individual absorbent assemblies 36. The bodyside liner 42, the individual absorbent assemblies 36 and the outer cover 44 combine to form a continuous web 46 which will advance in a machine direction (MD). The continuous web 46 has a primary stretch in a cross-direction (CD). The cross-direction is aligned approximately perpendicular to the machine direction (MD).

The bodyside liner 42 and the outer cover 44 can be formed from similar or different materials. The bodyside liner 42 and the outer cover 44 can each be formed from a stretch bonded laminate (SBL). A stretch bonded laminate is a material manufactured and commercially sold by Kimberly-Clark Corporation having an office at 401 North Lake Street, Neenah, Wis. 54956. Exemplary SBL materials are described in U.S. Pat. No. 4,720,415. In the stretch bonded laminate, the elastic core, or middle layer, is elongated before the two outer nonwoven layers are attached. The attachment can be by an adhesive, by heat, by pressure, by a combination of heat and pressure, or by any other means known to those skilled in the laminate art. Another material that can be used to construct the bodyside liner 42 or the outer cover 44 is a necked bonded laminate (NBL). The necked bonded laminate is also a three-layer laminate except that the elastic core, or middle layer, is not pre-stretched prior to being attached to the two outer nonwoven layers. The outer layers are necked stretched before the elastic core, or middle layer, is attached to them. Exemplary NBL materials are described in U.S. Pat. No. 5,336,545. Other examples of elastomeric materials that can be used to form the bodyside liner 42 and the outer cover 44 include: a continuous filament stretch bonded laminate (CFSBL) described in U.S. Pat. No. 5,385,775, a vertical filament laminate (VFL) described in U.S. Patent Publication 2002/0119722 A1 dated Aug. 29, 2002, a necked stretch bonded laminate (NSBL) and a necked thermal laminate (NTL). Combinations of the above materials, as well as other materials known to those skilled in the art, can also be used.

It should also be noted that the outer cover 44 can be constructed from an elastic film or laminate that is capable of being stretched in at least one direction. Desirably, the elastic film or laminate is capable of being stretched in at least two directions, desirably in the machine direction and in the cross direction. Alternatively, the bodyside liner 42 can be formed from an elastic nonwoven material that has a machine direction stretch. If machine direction stretch is required, the outer cover 44 may have to be cut and rotated before being aligned with the absorbent assembly 36. Various other stretchable and elastic materials, including laminates, are known to those skilled in the art and can also be used.

The second section 14 of the apparatus 10 further includes at least three of the following applicators for attaching or securing components to either the bodyside liner 42, to the individual absorbent articles 36 or to the outer cover 44. The first of such applicators is a surge material applicator 48 which is capable of applying a surge layer 50 adjacent to the bodyside liner 42 so that in the continuous web 46, the surge layer 50 will be positioned between the bodyside liner 42 and each of the individual absorbent assemblies 36. The surge layer 50 is desirably centrally located between the leading and trailing ends of each individual absorbent assembly 36 and is normally registered along the longitudinal axis thereof. The surge layer 50 functions to rapidly acquire and temporarily retain body fluid, such as urine, before it can be absorbed by the absorbent assembly 36. Desirably, the surge layer 50 is also capable of wicking body fluid lengthwise and/or widthwise across its surface, as well as directing the body fluid downward in the z-direction toward the absorbent assembly 36. Materials from which the surge layer 50 can be formed are well known to those skilled in the absorbency art.

A second of such applicators is a skin care applicator 52 which is capable of applying a skin care formulation or composition onto either the inner or outer surface of the bodyside liner 42, to each of the individual absorbent assemblies 36, to the surge layer 50 or to the inner or outer surface of the outer cover 44. Just for representative purposes, in FIG. 1, the skin care applicator 52 is depicted as applying a skin care formulation or composition onto the outer surface of the bodyside liner 42. The skin care formulation or composition can be a liquid, a solid or a semi-solid at room temperature. The formula or composition can be a variety of items including but not limited to aqueous solutions, ointments, lotions, creams, emulsions, etc. The composition or formulation can be any of a variety of skin treatments that can be delivered in effective amounts to a consumer's skin. Such skin treatments include but are not limited to alpha and/or beta hydroxyl-acids, analgesics, antimicrobials, antibodies, anti-acne, anti-irritants, antigens, anesthetics, anti-inflammatory substances, antioxidants, anti-adherents, anti-pruritic materials, astringents, botanicals, botanical extracts, buffers, chelators, cleansing compositions, emollients, exfoliants, proteins, lipids, carbohydrates, derivatives of each of the previous three items, enzymes, enzyme inhibitors, growth factors, irritant sequestrants, skin lightening agents, hair care compositions, depilatory compositions, shaving aids, fragrances, metal salts, microbial growth factors, microorganisms, odor absorbents, oxidizers, probiotics, moisturizers, muscle relaxants, lubricants, skin protectants, surfactants, vitamins, etc. These and other formulations or compositions can be delivered alone or in any number of permutations or combinations.

A third applicator is a containment flap applicator 54 which is capable of attaching or securing at least one pair of containment flaps onto the bodyside liner 42, to each of the individual absorbent assemblies 36 or to the outer cover 44. Desirably, the containment flaps (not shown) are located on the outer surface of the bodyside liner 42 and extend at least 50% of the length of the finished absorbent article. The pair of containment flaps is normally aligned approximately parallel with the longitudinal axis of the finished absorbent article and they are spaced apart from one another. The containment flaps are designed to stop and/or contain urine and/or bowel movement (BM) waste from escaping beyond the perimeter of the finished absorbent article. It should be noted that the containment flap applicator 54 could also form or manipulate the bodyside liner 42 to create bellows, folds, dams, raised members, etc., all of which can function to serve as containment flaps. The containment flaps can be formed out of separate pieces of material and can be either liquid permeable or liquid-impermeable. Alternatively, the containment flaps could be formed from the same material from which the bodyside liner 42 is constructed or from a different material. In addition, each containment flap can include one or more elastic strands aligned in the machine direction of the finished absorbent article. The elastic strand(s) can assist in causing the containment flaps to extend above the outer surface of the bodyside liner 42 when the absorbent article is being worn such that they contact the groin area of the wearer.

A fourth applicator is a side panel applicator 56 which is capable of attaching or securing at least one pair of side panels onto the bodyside liner 42, to each of the individual absorbent assemblies 36 or to the outer cover 44. Desirably, the side panels (not shown) are secured to both the bodyside liner 42 and to the outer cover 44 and can serve to extend the size of the waist opening in the finished absorbent article. Normally, side panels are located on the lateral sides of an absorbent article and bridge between the front and back panels. Very few absorbent articles actually employ side panels. A child training pant is one such absorbent article that may use side panels.

A fifth applicator is a leg elastic applicator 58 which is capable of applying one or more elastic strands to at least one layer or member of the continuous web 46 in a region where a pair of leg openings will later be formed in the continuous web 46. The leg elastics can be positioned adjacent to a portion of each leg opening or they can extend completely around each leg opening. One or more elastic strands can be applied, attached or secured to the continuous web 46. Normally, one, two or three elastic strands are spaced around at least a portion of each of the leg openings. The elastic strands are normally positioned in a parallel, spaced apart relationship to one another. Desirably, two or three elastic strands will be present in each leg region. The elastic strands can be secured to one or more layers of the continuous web 46 by using adhesives, ultrasonic energy, radiofrequency, or by heat and/or pressure bonding. The elastic strands can be elastomeric threads sold under the trade name LYCRA and are available from Invista having an office at 4123 East 37th Street North, Wichita, Kans. 67220.

The elastic strands can vary in size, shape, configuration and/or length. The diameter and/or cross-sectional configuration of the elastic strands, the decitex (weight in grams per 10,000 meters of a strand) of the elastic strands, and the tension imparted into the elastic strands can all be varied to suit one's particular needs. The elastic strands can have a round, semi-circular, square, rectangular, oval or some other geometrical configuration. The elastic strands can also be in ribbon form. The elastic strands can be aligned parallel to one another or be aligned to overlap, intersect or crisscross at least one other elastic strand. The various ways of positioning and orienting the elastic strands to one or more layers of the continuous web 46 are well known to those skilled in the art.

A sixth applicator is a crotch elastic applicator 60 which is capable of applying one or more elastic strands to at least one layer or member of the continuous web 46 in a crotch region of the finished absorbent article. The crotch elastic can be positioned adjacent to or be aligned on each side of the individual absorbent assembly 36 in a parallel and spaced apart configuration. The crotch elastics function to hold and retain the individual absorbent assembly and the bodyside liner 42 close to the groin area of the wearer such that body waste can be quickly and efficiently collected. One or more elastic strands can be applied, attached or secured to the continuous web 46. Normally, one, two or three elastic strands are spaced on each longitudinal side of the individual absorbent assembly. Desirably, two or three elastic strands will be present along each longitudinal side edge in the crotch region. The elastic strands can be secured to one or more layers of the continuous web 46 as explained above. The elastic strands can vary in size, shape, configuration and/or length as described above. Likewise, the crotch elastics can also be elastomeric threads sold under the trade name LYCRA.

A seventh applicator is a waist elastic applicator 62 which is capable of applying one or more elastic strands to the continuous web 46 at locations adjacent to the waist opening region of the finished absorbent article. The waist opening region is the region of the finished absorbent article that, when the article is worn, will surround the torso at approximately the belly button area of the wearer. The waist opening region can consist of the bodyside liner 42 being bonded or sealed, for example by a heat activated or heat shrinkable material, to the outer cover 44. The waist opening elastics normally consist of 2 to 12 elastic strands, desirably 4 to 6 elastic strands that completely encircle the waist opening and are arranged in a parallel and spaced apart configuration, Commonly, the elastic strands of the waist opening are spaced less than 8 millimeters apart. The waist opening elastics function to form an elastic waist band that assist in holding the finished absorbent article firmly against the torso of the wearer. The waist opening elastics can be positioned between the bodyside liner 42 and the outer cover 44 or be secured to an outer surface of either member. The waist opening elastics normally extend in a horizontal direction around at least a major portion of the circumference of the finished absorbent article. The elastic strands can be secured to one or more layers of the continuous web 46 as explained above. The elastic strands can vary in size, shape, configuration and/or length as described above. Likewise, the waist opening elastics can be elastomeric threads sold under the trade name LYCRA or be formed from a heat activated material.

An eighth applicator is a waist panel applicator 64 which is capable of forming at least one containment pocket. This waist panel applicator 64 can be utilized along with the waist elastic applicator 62 to manufacture certain absorbent articles, such as infant care diapers. The containment pockets serve to catch any body waste that may try to escape from the ends of the finished absorbent article. Such containment pockets are usually utilized in infant diapers where the bowel movement tends to produce very liquid or running excrement. The waist panel applicator 64 is capable of forming one or two containment pockets on an upper surface of the finished absorbent article. Each pocket is normally positioned adjacent to an end of the finished absorbent article. When two containment pockets are utilized, they are normally constructed at the opposite ends of the finished absorbent article. The containment pockets can be formed by attaching a strip of material across the width of the bodyside liner 42 such that it is secured along the two longitudinal side edges and at the distal end. The inner end of each containment pocket, that is, the end closest to the transverse centerline of the finished absorbent article, is left unattached such that waste material deposited onto the finished absorbent article can flow or move into one of the containment pockets. The presence of the containment pockets at each end of the finished absorbent article will prevent such waste material from escaping from the absorbent article and soiling the legs or torso of the wearer.

It should be noted that the apparatus 10 can include one or more pressure bonders, nip bonders and other kinds of mechanisms to ensure that the attached components and the elastic strands are securely applied and/or adhered to the continuous web 46. These commonly used mechanisms are not depicted in FIG. 1 since they are well known to those skilled in the art and may be employed at various locations depending on the type of absorbent article being manufactured.

A ninth applicator is a fastener applicator 66 which is capable of engaging one or more fasteners, such as hooks or loop fasteners, adhesive tape, VELCRO, or other known types of mechanical fasteners to the continuous web 46. Certain absorbent articles, such as a child training pant and an adjustable adult incontinent undergarment, utilize such fasteners so that the article can be opened and closed about the waist of the wearer. These fasteners are normally applied to the continuous web 46 at locations adjacent to the waist opening region in the finished absorbent article. As stated above, the fasteners allow the wearer or a caregiver to open and inspect the absorbent article and then reattach the fasteners so that the absorbent article can continue to be used for its intended purpose. Some fasteners also allow the absorbent article to be adjusted so that it fits better about the torso of the wearer.

A tenth applicator is an ear applicator 68 which is capable of applying one or more ears onto the continuous web 46. The ear applicator 68 is primarily utilized in infant diapers where ears are common. Normally, an ear is attached to each longitudinal side edge approximate either the front or back panel. Each ear extends outward away from the respective longitudinal side edge of the absorbent article. Each ear can contain a landing zone which provides an area into which a fastener can attach so as to convert an open product into a closed absorbent article that surrounds the torso of the user. Infant diapers are absorbent articles that are commonly manufactured and sold as open products since a mother, father or caregiver is required to attach and/or remove the absorbent article from an infant's body. It is easier to position an open article around the infant's torso, since most infants are changed while lying on their backs, than to try to slip a closed or unitary absorbent article up over their legs. The ears can vary in size, shape and location but normally are attached adjacent to the waist opening region of the absorbent article.

An eleventh applicator is a front and back leg elastic applicator 70 which is capable of applying one or more elastic strands, one or more pieces of elastic material or one or more pieces of heat shrinkable material to a large absorbent article, such as an adult incontinent undergarment. These large absorbent articles require extra protection about the leg openings to prevent fluid leakage from occurring. The leg elastics can be positioned on the front panel and on the back panel adjacent to a portion of each leg opening. One or more elastic strands can be applied, attached or secured to the continuous web 46. Normally, one, two or three elastic strands or pieces of elastic material are utilized. With reference to elastic strands, they are usually applied so that they extend inward from the longitudinal side edges toward the longitudinal centerline of the absorbent article. The elastic stands are normally positioned in a parallel, spaced apart relationship to one another. Desirably, two or three elastic strands will be present in each of the front and back panels within about 0.25 inches (about 0.6 cm) of each of the leg openings. The elastic strands can be secured to one or more layers of the continuous web 46 as described above. The front and back leg elastics can be elastomeric threads sold under the trade name LYCRA or be formed from a heat activated material.

A twelfth applicator is a leg cut out applicator 72 which is capable of cutting out leg openings in the continuous web 46. Normally, a semi-circular or some other geometrical shape is cut out of the continuous web 46 so that the absorbent article acquires an hourglass shaped appearance. The region between the leg cut outs is referred to as the crotch region. The leg cut out applicator 72 can cut the bodyside liner 42, the outer cover 44 as well as a portion of the individual absorbent assemblies 36, if desired.

Turning now to the third section 16 of the apparatus 10, one will see that this section also includes several applicators. The third section 16 includes a cutting applicator 74 which is capable of severing or separating the continuous web 46 into individual absorbent articles 76. The cutting applicator 74 can slice, cut or separate the continuous web 46 in the cross-direction so that each individual absorbent article 76 has a predetermined length. The cut can be made perpendicular to the longitudinal central axis of the continuous web 46 or at an angle thereto. The third section 16 further includes a number of additional applicators of which at least three are needed to be present and activated in order to manufacture a particular individual absorbent article 76. One such applicator is a first folding applicator 78 which is capable of folding each of the individual absorbent articles 76 in half such that the front panel overlaps the back panel. A second of such applicators is a hook fastening applicator 80 which is capable of fastening any hooks or attachment members that may have been applied by the fastener applicator 66. The hooks or attachment members can be fastened to themselves or to some other portion of the individual absorbent articles 76 so that they are ready to be opened and utilized when the absorbent article 76 is to be worn. A third applicator is a bonding applicator 82 which is capable of bonding the front panel to the back panel. The bonding applicator 82 is capable of forming a pair of side seam bonds which produce a closed or unitary absorbent article. A closed or unitary absorbent article needs to be pulled up along the wearer's legs and onto the wearer's torso in a similar fashion as cotton underwear.

The third section 16 also includes an ear folding applicator 84 which is capable of folding any ears that may have been applied by the ear applicator 68. The ears can be folded upon themselves or over a portion of the individual absorbent articles 76.

Another applicator in the third section 16 is a panel tucking applicator 86 which is capable of tucking a portion of the lateral sides of the front and back panels into the individual absorbent articles 76. This action will decrease the overall width of the individual absorbent articles 76 and is utilized primarily for closed or pre-fastened absorbent articles such as child training pants and adult incontinent undergarments.

The third section 16 further includes a second folding applicator 88 which is capable of folding each of the individual absorbent articles 76 a second time in a predetermined manner. This second fold can be in the longitudinal or transverse direction of the individual absorbent articles 76. Normally, only large absorbent articles, such as adult incontinent undergarments, need to be folded a second time. It should be noted that additional folding applicators can be utilized in the apparatus 10 if needed.

The third section 16 further includes a heating applicator 90 which is capable of causing at least some of the elastic strands, elastic material or heat shrinkable material to contract due to the application of heat. The amount of heat applied and the time period over which the heat is present can be adjusted to suit one's specific product specifications. The heat can be applied to localized areas of the individual absorbent articles 76 or to the entire individual absorbent articles 76. The elastic strands, elastic material or heat shrinkable material subjected to the heat will contract and give the absorbent article a corrugated appearance around the waist opening and around the pair of leg openings. The contraction of the elastic strands, elastic material or heat shrinkable material and the formation of corrugations at these locations will assist in preventing fluid leakage from the individual absorbent articles 76.

The third section 16 still further includes a stacking applicator 92 which is capable of arranging the individual absorbent articles 76 into one or more orderly piles. Each pile can contain a number of vertically oriented absorbent articles 76. Each pile can contain from between about 2 to about 50 absorbent articles 76 depending upon the size and shape of such articles. Desirably, each pile will contain from between about 5 to about 30 absorbent articles 76. Even more desirably, each pile will contain from between about 5 to about 20 absorbent articles 76. Alternatively, the stacking applicator 92 can arrange the individual absorbent articles into horizontally oriented stacks.

A packaging applicator 94 is also present which is capable of inserting one or more piles into a package 96 and closing and sealing the package 96. Alternatively, the packaging applicator 94 can be a mechanism capable of wrapping material around the one or more piles to form a package. When a conventional package 96 is being formed, it can be constructed as a cardboard box, a flexible plastic bag, a paper bag, etc. Any type of packaging material known to those skilled in the packaging art can be utilized.

Various disposable absorbent articles such as infant diapers, child training pants, menstrual pants, adult incontinent undergarments, guards for men, incontinent briefs, etc., can be manufactured using the apparatus 10. The method utilizing the apparatus 10 will vary depending upon what particular absorbent article the manufacturer wishes to produce. For example, in the manufacture of infant diapers, the barrier material applicator 30, the skin care applicator 52, the containment flap applicator 54, the waist panel applicator 64, the ear applicator 68 and the ear folding applicator 84 may be needed and activated. However, the side panel applicator 56, the front and back leg elastic applicator 70, the hook fastening applicator 80, the bonding applicator 82, the panel tucking applicator 86 and the second folding applicator 88 may not be needed or may be optional. The applicators that are not needed or desired can be turned off or deactivated.

In the manufacture of a child training pant, the barrier material applicator 30, the containment flap applicator 54, the side panel applicator 56, the fastener applicator 66, the hook fastening applicator 80 and the panel tucking applicator 86 may be needed and activated. However, the skin care applicator 52, the waist panel applicator 64, the ear applicator 68, the front and back leg elastic applicator 70, the ear folding applicator 84, and the second folding applicator 88 may not be needed or may be optional. The applicators that are not needed or desired can be turned off or deactivated.

In the manufacture of an adult incontinent undergarment, the barrier material applicator 30, the front and back leg elastic applicator 70, the panel tucking applicator 86 and the second folding applicator 88 may be needed and activated. However, the skin care applicator 52, the containment flap applicator 54, the side panel applicator 56, the waist panel applicator 64, the fastener applicator 66, the ear applicator 68, the hook fastening applicator 80, and the ear folding applicator 84 may not be needed or may be optional. The applicators that are not needed or desired can be turned off or deactivated.

The remaining applicators may be needed and activated for all three absorbent article styles. For example, the odor control applicator 22, the superabsorbent applicator 24, the fluff former applicator 26, the surge material applicator 48, the leg elastic applicator 58, the crotch elastic applicator 60, the waist elastic applicator 62, the leg cut out applicator 72, the first folding applicator 78, the heating applicator 90, the stacking applicator 92 and the packaging applicator 94 may be needed or desired for all three absorbent article styles.

METHOD

The method of manufacturing several distinct disposable absorbent articles on a single machine includes forming an absorbent assembly 18 and cutting the absorbent assembly into individual absorbent assemblies 36, each having a predetermined size and shape. A bodyside liner 38 is then aligned with the individual absorbent assemblies 36 and both are advanced in a machine direction (MD). An outer cover 40 is applied to the individual absorbent assemblies 36, on an opposite surface to the bodyside liner 42 and all three layers form a continuous web 46. The continuous web 46 has a primary stretch in a cross-direction. Then at least three components are added or attached to the continuous web 46 or to at least one layer of the continuous web 46. The three components are selected from the following group of options: a surge layer 50, a skin care formulation or composition, at least one pair of containment flaps, at least one pair of side panels, elastics which will correspond to at least one of the following regions of each of the individual absorbent articles 76: a crotch region, a waist region and leg opening regions; at least one pair of ear panels and at least one fastener. The continuous web 46 is then severed in a cross-direction to form individual absorbent articles 76. These individual absorbent articles 76 are then folded at least once and stacked into one or more orderly piles. The piles are then inserted into a package or have a package formed around them. When a conventional package 96 is formed, it can be sealed such that it is now ready to be shipped to a retailer.

The method can be modified or adjusted so as to form individual absorbent articles, such as absorbent pads, instead of forming a continuous web and then cutting the web to obtain individual absorbent articles.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A method of manufacturing several distinct disposable absorbent articles on a single machine, said method comprising the steps of:
   a) forming an absorbent assembly having at least one absorbent layer and cutting said absorbent assembly into individual absorbent assemblies each into a predetermined size and shape;
   b) moving a bodyside liner into alignment with said individual absorbent assemblies and applying an outer cover to said individual absorbent assemblies to form a continuous web having a primary stretch in a cross-direction;
   c) adding at least one of the following components to either said bodyside liner, said individual absorbent assemblies or to said outer cover by activating certain applicators at a predetermined time: a surge layer, a skin care formulation, at least one pair of containment flaps, at least one pair of side panels, elastics which will correspond to at least one of the following regions of each of said individual absorbent articles: a crotch region, a waist region and leg opening regions, at least one pair of ear panels, and at least one fastener;
   d) cutting a pair of leg openings in said web;
   e) severing said continuous web in a cross-direction to form individual absorbent articles;
   f) folding said individual absorbent articles at least once;
   g) stacking said folded absorbent articles into at least one orderly pile; and
   h) wrapping a package around said one or more orderly piles.

2. The method of claim 1 further including folding said individual absorbent articles a second time.

3. The method of claim 1 used to manufacture an infant diaper.

4. The method of claim 1 used to manufacture a child training pant.

5. The method of claim 2 used to manufacture an adult incontinent undergarment.

* * * * *